United States Patent
Fukao et al.

(10) Patent No.: US 6,252,068 B1
(45) Date of Patent: Jun. 26, 2001

(54) PROCESS FOR PRODUCING ε-CAPROLACTAM

(75) Inventors: Masami Fukao, Shiga; Kan Takamine, Osaka, both of (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/472,172

(22) Filed: Dec. 27, 1999

(30) Foreign Application Priority Data

Dec. 28, 1998 (JP) .................................................. 10-371842

(51) Int. Cl.⁷ .................................................. C07D 201/16

(52) U.S. Cl. .......................................................... 540/540

(58) Field of Search .............................................. 540/540

(56) References Cited

U.S. PATENT DOCUMENTS

| 3,966,712 | 6/1976 | Immel et al. ................ | 260/239.3 A |
| 4,148,792 | 4/1979 | Danziger et al. ............ | 260/239.3 A |
| 5,362,870 | 11/1994 | Higashio et al. ............ | 540/540 |
| 5,502,184 | 3/1996 | Kajikuri et al. ............ | 540/536 |

FOREIGN PATENT DOCUMENTS 848666A  2/1996  (JP) .

*Primary Examiner*—Bruck Kifle
(74) *Attorney, Agent, or Firm*—Birch, Stewart, Kolasch and Birch, LLP

(57) ABSTRACT

A high purity ε-caprolactam is prepared by crystallizing an ε-caprolactam from a hydrocarbon solution containing a crude ε-caprolactam, and allowing the crystallized ε-caprolactam in contact with hydrogen in the presence of a hydrogenation catalyst. This process can effectively remove impurities from a crude ε-caprolactam, which is obtained by subjecting cyclohexanone oxime to the Beckmann rearrangement, and provide a high purity ε-caprolactam.

11 Claims, No Drawings

PROCESS FOR PRODUCING ε-CAPROLACTAM

FIELD OF THE INVENTION

The present invention relates to a process for purifying and producing ε-caprolactam. In particular, the present invention relates to a process for purifying and producing ε-caprolactam comprising the steps of crystallizing an ε-caprolactam from a solution containing a crude ε-caprolactam obtained by any kinds of reaction such as the Beckmann rearrangement of cyclohexanone oxime and allowing the crystallized ε-caprolactam in contact with hydrogen in the presence of a hydrogenation catalyst.

BACKGROUND OF THE INVENTION

ε-Caprolactam is an important compound as an intermediate for the preparation of polyamides such as Nylon-6, and many processes are known to produce ε-caprolactam. For example, ε-caprolactam can be commercially produced by subjecting cyclohexanone oxime to the Beckmann rearrangement in the presence of an acidic medium such as fuming sulfuric acid. However, this process has drawbacks such that a large amount of ammonium sulfate, which has a less added value, is produced as a by-product.

As a process which can improve the above process, a gas phase Beckmann rearrangement using a solid catalyst is known to produce ε-caprolactam. The proposed solid catalysts used in the gas phase Beckmann rearrangement include boric acid catalysts, silica-alumina catalysts, solid phosphoric acid catalysts, complex metal oxide catalysts, zeolite catalysts, etc. Furthermore, JP-A-62-123167 and JP-A-63-54358 disclose the use of high silica metallosilicate catalysts for the production of ε-caprolactam.

Processes for producing ε-caprolactam, which is not based on the Beckmann rearrangement, are also known. For example, JP-A-2-215767 discloses a process comprising the steps of cycling methyl 6-aminocaproate to obtain ε-caprolactam, U.S. Pat. No. 5,495,016 discloses a process comprising the step of reacting 6-aminocapronitrile with water to obtain ε-caprolactam, and JP-A-9-3041 discloses a process comprising the step of reacting methyl 6-hydroxycaproate with ammonia in the presence of hydrogen and steam to obtain ε-caprolactam.

However, ε-caprolactam obtained by such processes contains various impurities. As is well known, ε-caprolactam is used as a raw material for the preparation of polyamide, and ε-caprolactam used to prepare polyamide, which is in turn used to produce synthetic fibers or films, is required to have high purity. Thus, the crude ε-caprolactam prepared by the above processes is first purified by various purification methods, and then the high purity ε-caprolactam is used to prepare polyamide for producing a product such as synthetic fibers or films.

As the purification methods, many methods are known as follows:

Distilling a crude ε-caprolactam which is obtained by rearranging cyclohexanone oxime in a sulfuric acid medium by a rectifying method (APPLIED ORGANIC CHEMISTRY, page 244 (published by TOKYO KAGAKU DOJIN in 1989);

Dissolving a crude ε-caprolactam in an organic solvent such as toluene or dimethylformamide, and crystallizing ε-caprolactam (JP-A-53-37687, JP-A-49-54389, JP-A-46-5231, etc.);

Mixing a crude ε-caprolactam with a hydrocarbon and water, separating the mixture, and extracting the ε-caprolactam with water (JP-B-36-14119, JP-A-5-294925, etc.);

Ion exchanging a crude ε-caprolactam;

Allowing a crude ε-caprolactam in contact with hydrogen at a temperature of from 100° C. to 200° C. in the presence of a hydrogenation catalyst (JP-A-7-109255).

However with the purification method such as distillation, crystallization, extraction or ion exchange, impurities having similar chemical properties to those of ε-caprolactam or by-products having boiling points close to that of ε-caprolactam cannot be removed sufficiently. In particular, compounds having a similar chemical structure to that of ε-caprolactam and having one carbon-carbon double bond in a molecule, such as 1,3,4,5-tetrahydroazepin-2-on, 1,5,6,7-tetrahydroazepin-2-on, and the like (hereinafter, generally referred to as "caprenolactams") cannot be removed, and thus deteriorate the quality of ε-caprolactam.

According to the observation of the researches of the present inventors, it has been found that the caprenolactams severely deteriorate the quality of ε-caprolactam. In concrete, it is found that, when an ε-caprolactam containing about 30 ppm or more of the caprenolactams is used as a raw material for producing polyamide, various problems may arise. Therefore, it is necessary to sufficiently remove the caprenolactams from the ε-caprolactam in order to obtain an ε-caprolactam having high qualities from the industrial point of view.

The present inventors have also found that the hydrogenation process is a very advantageous process since the caprenolactams are hydrogenated and converted to ε-caprolactam and a crude ε-caprolactam can be simultaneously purified, and furthermore the caprenolactams are effectively utilized. However, in the hydrogenation process, not only the caprenolactams but also by-products other than the caprenolactams participate in the hydrogenation reaction. Thus, much loading tends to be put on the hydrogenation catalyst. Therefore, the reaction efficiency decreases, and the life of the catalyst is shortened. In consequence, a crude ε-caprolactam cannot be economically treated for a long time with the hydrogenation process.

As explained above, the conventional purification methods such as distillation, crystallization, extraction, ion exchange, hydrogenation, etc. are not always satisfactory to obtain an ε-caprolactam having an industrially required purity, when the easiness of process operation and costs are taken into account.

SUMMARY AND OBJECTS OF THE INVENTION

The present inventors have made extensive researches with the object of providing a process for producing ε-caprolactam having an industrially required high quality by removing by-products from a crude ε-caprolactam in an efficient and economical way. As a result, it has been found that such an ε-caprolactam can be obtained by a specific combination of purification methods. The present invention has been accomplished on the bases of the above findings.

Accordingly, the present invention provides a process for purifying ε-caprolactam comprising the steps of:

crystallizing an ε-caprolactam from a hydrocarbon solution containing a crude ε-caprolactam, and allowing the crystallized ε-caprolactam in contact with hydrogen in the presence of a hydrogenation catalyst.

Furthermore, the present invention provides a process for producing ε-caprolactam comprising the steps of:

crystallizing an ε-caprolactam from a hydrocarbon solution containing a crude ε-caprolactam, and allowing the crystallized ε-caprolactam in contact with hydrogen in the presence of a hydrogenation catalyst.

DETAILED DESCRIPTION OF THE INVENTION

In the present invention, a high quality ε-caprolactam can be obtained by crystallizing an ε-caprolactam from a hydrocarbon solution containing a crude ε-caprolactam, and then allowing the crystallized ε-caprolactam in contact with hydrogen in the presence of a hydrogenation catalyst.

A method for the preparation of a crude ε-caprolactam is not limited in the present invention. The advantages of the process of the present invention are remarkable when a crude ε-caprolactam which is obtained by the gas phase Beckmann rearrangement in the presence of a zeolite type catalyst such as metallosilicate or in the presence of silicalite. This is because impurities in the crude ε-caprolactam, such as cyclohexanone oxime, caprenolactams, 1,2,3,4,6,7,8,9-octahydrophenazine (hereinafter, referred to as "OHP") and 3-N-methyl-4,5,6,7-tetrahydrobenzimidazole (herein after, referred to as "MTHI", can be sufficiently removed with the process of the present invention. That is, when an ε-caprolactam is produced by combining the process of the present invention with the gas phase Beckmann rearrangement using a zeolite type catalyst, a high quality ε-caprolactam can effectively be obtained at a low cost.

When a reaction mixture containing ε-caprolactam which is obtained by the gas phase Beckmann rearrangement using a zeolite type catalyst is used as a source of a crude ε-caprolactam in conducting the process of the present invention, the crude ε-caprolactam may sometimes contain a solvent such as alcohol in addition to the above impurities. Thus, it is preferable to preliminarily distill the reaction mixture prior to crystallization, if necessary.

The crystallization in the process of the present invention is preferably carried out using a hydrocarbon solvent having a low polarity. When water or an organic solvent having a high polarity is used, ε-caprolactam is dissolved in such a solvent, and thus the yield of ε-caprolactam tends to decrease. In this case, it is difficult to recover ε-caprolactam dissolved in the solvent.

Examples of the solvents used in the crystallization step include linear aliphatic hydrocarbons having 6 to 12 carbon atoms, side-chain aliphatic hydrocarbons having 6 to 12 carbon atoms, alicyclic hydrocarbons having 6 to 12 carbon atoms, etc. Specific examples of such solvents include linear aliphatic hydrocarbons such as hexane, heptane, octane, nonane and decane; side-chain aliphatic hydrocarbons such as methylhexane, isooctane and neohexane; and alicyclic hydrocarbons such as methylcyclopentane, cyclohexane and methylcyclohexane. Among them, cyclohexane, heptane and isooctane are preferable. These solvents may be used singly or in admixture of two or more of them. An aromatic hydrocarbon such as benzene, toluene and xylene may be utilized in a small amount together with the above solvents as long as the removal of the impurities is not interfered.

An amount of the solvent used for crystallization is from about 0.5 to about 5 parts by weight, preferably from about 1 to about 4 parts by weight, based on one part by weight of ε-caprolactam. Even when the amount of solvent exceeds the above upper limit, the crystallizing effects are not improved in proportion to the increased amount of solvent, and costs to recover the solvent increase. When the amount of solvent is too small, the impurities may not sufficiently be removed.

Examples of the methods for crystallizing ε-caprolactam include a method comprising the steps of mixing a crude ε-caprolactam in the molten state with the above solvent, and then cooling the mixture while stirring, a method comprising the step of mixing a crude ε-caprolactam in the molten state with a cooled solvent, and the like. With such a crystallization, almost all the impurities (except caprenolactams) contained in a crude ε-caprolactam can be expelled to the solvent. After crystallization, the obtained crystal is separated from the solvent by a suitable method such as filtration, sedimentation, etc. Optionally, the obtained crystal may be washed with the above solvent.

A crystallization temperature may be from about 10° C. to less than the melting point of ε-caprolactam, preferably from about 30° C. to about 60° C., more preferably from about 40° C. to about 60° C.

In the process of the present invention, an ε-caprolactam is first obtained by crystallization, and then the crystallized ε-caprolactam is hydrogenated. It is preferable that the contents of the impurities such as cyclohexanone oxime, MTHI and OHP are decreased to specific amounts or less after the crystallization. Such contents of impurities may be expressed by a free basicity of the crude ε-caprolactam obtained after crystallization, since cyclohexanone oxime, MTHI, OHP, etc. are basic compounds. It is preferable to purify the crude ε-caprolactam with crystallization so that the free basicity thereof is decreased to about 1 meq/kg or less, more preferably about 0.25 meq/kg or less. The contents of the impurities may also be expressed by a pH value of the crude ε-caprolactam. For example, when crystallization of ε-caprolactam is conducted to such an extent that a solution obtained by dissolving 0.25 g of the crystallized ε-caprolactam in 1 ml of water, wherein the water in itself is prepared to have pH of 5.7, has a pH vale of 6.5 or less, the remaining impurities in the crystallized ε-caprolactam can be readily and effectively removed in the subsequent hydrogenation step to provide a high quality ε-caprolactam.

ε-Caprolactam after crystallization may contain a small amount of a solvent used in the crystallization step. The amount of the remaining solvent is preferably about 10% by weight or less based on ε-caprolactam.

To achieve the above degree of the removal of impurities by crystallization, a kind and an amount of a solvent used, and crystallization conditions such as a temperature are properly selected. Such conditions can be set by preliminary experiments, and the like. The crystallization is usually carried out one or more times, while it is recommended to repeat the crystallization two or more times when the crude ε-caprolactam utilized contains a large amount of impurities.

After crystallization, ε-caprolactam is subjected to a subsequent hydrogenation. ε-Caprolactam to be hydrogenated preferably has a free basicity of 1 meq/kg or less, more preferably 0.25 meq/kg or less, or a pH value of 6.5 or less, which is measured as described above. By subjecting such a crystallized ε-caprolactam to the hydrogenation, the contents of impurities in ε-caprolactam can be decreased to less than 10 ppm of cyclohexanone oxime, less than 10 ppm of OHP, less than 25 ppm of MTHI, and less than 30 ppm of caprenolactams.

The hydrogenation can be carried out by a conventional method. For example, as a catalyst, a transition metal of the VIII group (e.g. palladium, platinum, ruthenium, rhodium, etc.), which is supported on a carrier (e.g. activated carbon, alumina, silica, titania, etc.), maybe used. Among them, an eggshell type supported catalyst which carries palladium alone, or palladium and other metal such as platinum or ruthenium on the carrier surface are preferable in view of its catalytic activity or its life span. When the supported catalyst is used, the amount of a metal catalyst to be supported is preferably from about 0.1% to about 20% by weight, more preferably from about 0.5% to about 5% by weight, in terms of the weight of a metal, based on the weight of the supported catalyst. In the case of an eggshell type one, the amount of a co-supported metal such as platinum or ruthenium is preferably from about 0 to about 2% by weight based on the weight of the supported catalyst.

In the hydrogenation step, water or an organic solvent may optionally be used. The crystal of ϵ-caprolactam obtained from the crystallization step may contain a small amount of a remaining solvent which is used in the crystallization step. The remaining solvent may optionally be removed prior to the hydrogenation. When a solvent is used in the hydrogenation step, it should be separated to collect ϵ-caprolactam.

In the hydrogenation step, ϵ-caprolactam in a melt state may be supplied together with hydrogen to a catalyst layer in which ϵ-caprolactam is hydrogenated.

A reaction mode may be a batch process, a continuous process or a fixed bed process. In the case of a fixed bed process, a supply manner may be an upflow or a down flow, or a counter flow. In an industrial production, the fixed bed process is preferable from the viewpoint of operability and costs.

A reaction temperature in the hydrogenation step using no solvent is at least the melting point of ϵ-caprolactam, preferably from about 70° C. to about 150° C., since ϵ-caprolactam should be melted. When a solvent is used, a reaction temperature may be at least a temperature at which ϵ-caprolactam is dissolved in the solvent.

When ϵ-caprolactam is continuously hydrogenated, the catalytic activity of a catalyst gradually tends to decrease as the time passes. Thus, it is preferable to increase a reaction temperature as the catalytic activity decreases to maintain the catalytis activity at a certain level, so as to stabilize the quality of produced ϵ-caprolactam. In this purpose, it is preferred that the reaction temperature in the initial stage of the reaction is relatively low, for example, from about 70° C. to about 80° C., and then the reaction is continuously carried out while gradually increasing the reaction temperature.

A reaction pressure in the hydrogenation step is not limited, and is usually from about 0.5 to about 100 kg/cm$^2$ (about 0.05 to 6 about 10 MPa), preferably from about 2 to about 10 kg/cm$^2$ (about 0.2 to about 1 MPa).

The amount of hydrogen, which can be dissolved in the melt of ϵ-caprolactam, is not sufficient to hydrogenate ϵ-caprolactam. An amount of hydrogen gas for hydrogenation is preferably at least the equimolar amount to the caprenolactams obtained in ϵ-caprolactam. In general, the amount of hydrogen gas may be at least about 0.001 mole, preferably from about 0.01 to about 0.25 mole, per 1 mole of ϵ-caprolactam. The unreacted hydrogen gas may be recycled.

When the reaction mode is a fixed bed process, a space velocity WHSV of the utilized ϵ-caprolactam is usually from about 0.5 to about 100 h$^{-1}$, preferably from about 0.5 to 30 h$^{-1}$, more preferably from about 1 to about 10 h$^{-1}$.

And a period of contact time of ϵ-caprolactam and a catalyst is preferably in the range of 0.033 to 2 hours. It is noted that a space velocity WHSV can be defined as the following equation; WHSV (h$^{-1}$)=[a weight of the ϵ-caprolactam fed into catalyst (kg/h)]/[a weight of catalyst (kg)]. The life of a catalyst may depend on the raw material, reaction conditions, etc. In the process of the present invention, the life of the catalyst can be prolonged to one year or longer.

After the hydrogenation, ϵ-caprolactam may be distilled, if necessary. The distillation can remove the remaining solvent which is used in the crystallization step, and the like.

According to the process of the present invention, ϵ-caprolactam containing less than 10 ppm of cyclohexanone oxime, less than 10 ppm of OHP, less than 25 ppm of MTHI, and less than 30 ppm (preferably less than 25 ppm) of caprenolactums can be obtained.

When a potassium permanganate value (PM value) is used as an indicator which indicates the amount of impurities remaining in ϵ-caprolactam, an ϵ-caprolactam usually obtained by the process of the present invention can be evaluated to have a PM value of less than about 10, while it is possible in the present invention to obtain high-quality ϵ-caprolactam having a PM value of less than about 7.

According to the process of the present invention, the combination of simple steps such as crystallization and hydrogenation can effectively remove by-products from a crude ϵ-caprolactam at low costs, and provides a high quality ϵ-caprolactam, which can be used as a raw material of the industrial production of polyamide, that is, an ϵ-caprolactam containing less than 10 ppm of cyclohexanone oxime, less than 10 ppm of OHP, less than 25 ppm of MTHI, and less than 30 ppm (preferably less than 25 ppm) of caprenolactums.

The process of the present invention can attain a higher yield of the product than conventional methods in which distillation or crystallization is repeated. In addition, the process of the present invention puts a less loading on a catalyst in the hydrogenation step, and thus prolongs the life of the catalyst.

EXAMPLES

The present invention is illustrated by the following Examples, which do not limit the scope of the invention in any way.

The following measurements was used in Examples to evaluate the qualities of the obtained ϵ-caprolactam:

Purity of ϵ-caprolactam and contents of impurities therein

The purity of ϵ-caprolactam and the contents of impurities in ϵ-caprolactam were measured with gas chromatography. The limit of detection of impurities was 3 ppm.

UV ray transmittance

ϵ-Caprolactam (1.13 g) was dissolved in water to make 10 ml of the solution, and then a transmittance through the solution of UV ray having a wavelength of 290 nm or 315 nm was measured using water as a reference solution.

Potassium permanganate value (PM value)

ϵ-Caprolactam (1 g) was dissolved in distilled water to make 100 ml of the solution. To this solution, a 0.01 N aqueous solution of potassium permanganate (2 ml) was added and the resulting solution was well stirred. After 250 seconds from the addition of the solution of potassium permanganate, the absorbance of the solution with a light having a wavelength of 420 nm was measured at a solution temperature of 25° C.

Separately, a solution consisting of distilled water and the aqueous solution of potassium permanganate was prepared as a reference solution and the absorbance thereof with light having a wavelength of 420 nm was measured.

The absorbance of the solution of potassium permanganate was subtracted from the absorbance of the solution of ϵ-caprolactam, and the obtained value was multiplied by 100 to obtain the potassium permanganate (PM) value of the ϵ-caprolactam.

Free basicity (FB)

pH of distilled water was adjusted to 5.7 by the addition of 0.01 N sulfuric acid or 0.01 N aqueous sodium hydroxide. To such distilled water (10 ml), ε-caprolactam (about 10 g) was added and the resulting solution was stirred. Then, pH of the resulting solution was measured. If the pH thereof is larger than 5.7, 0.01 N sulfuric acid was added to the solution until pH reaches 5.7.

A free basicity (meq/kg) was calculated from the consumed amount (v:ml) of 0.01 N sulfuric acid, the factor (f) of sulfuric acid, and the weight (w:g) of the ε-caprolactam utilized, based on the following equation:

$$FB \text{ (meq/kg)} = (0.01 \times v(\text{ml}) \times f \times 1000)/w(g)$$

pH value pH of distilled water was adjusted to 5.7 by the addition of a dilute sulfuric acid or a dilute aqueous sodium hydroxide. To such distilled water (1 ml), ε-caprolactam (0.25 g) was added and the resulting solution was stirred. Then, pH of the resulting solution was measured.

Volatile basicity (VB)

ε-Caprolactam (about 5 g) and a 20% aqueous sodium hydroxide (8 ml) were charged in a distillation flask, and then were steam-distilled. The effluent therefrom was introduced in a 0.01 N sulfuric acid (5 ml). The distillation was terminated when the amount of the effluent reached 150 ml.

The obtained solution was titrated with a 0.01 N aqueous sodium hydroxide using a mixture of methyl red and methylene blue as an indicator.

A volatile basicity VB (ppm) was calculated from the above obtained titer B (ml), a titer A (ml) in a blank test using no ε-caprolactam, a factor (f') of the utilized 0.01 N aqueous sodium hydroxide and the weight of the ε-caprolactam utilized (w':g), based on the following equation:

$$VB \text{ (ppm)} = [0.17 \times (B-A) \times f' \times 1000]/w'(g)$$

EXAMPLE 1

Into a fluidized layer reactor packed with a high silica zeolite catalyst, a liquid mixture of cyclohexanone oxime, methanol and water (weight ratio of 1:1.8:0.052) was introduced together with a nitrogen gas through a vaporizer, and was subjected to a Beckmann rearrangement under the conditions of a reaction temperature of 380° C. and a retention time of 8 seconds. The reaction gas was cooled and trapped to obtain a reaction mixture containing an ε-caprolactam.

This reaction mixture was distilled to remove methanol, low-boiling impurities and high-boiling impurities to obtain a crude ε-caprolactam having a purity of 98.97%, which contained 584 ppm of cyclohexanone oxime, 604 ppm of MTHI, and 355 ppm of OHP according to GC analysis.

Into a 200 liter reactor, the obtained crude ε-caprolactam after distillation (31.28 kg), and a mixed solvent of cyclohexane and n-heptane (weight ratio of 1:3) (46.92 kg) were charged, and were heated to 70° C. to dissolve ε-caprolactam in the solvent, followed by cooling to 60° C. while stirring. Then, a slight amount of ε-caprolactam crystal was added to the solution as a seed crystal. The mixture was stirred for 30 minutes, was cooled to 50° C. over 1 hour, and was stirred for another 30 minutes to precipitate an ε-caprolactam. The precipitated ε-caprolactam crystal was recovered by filtration, and was washed at about 40° C. with the above-utilized kind of mixed solvent (31.28 kg) as described above, to obtain a crystalline ε-caprolactam (29.65 kg). The yield was 94.8%. The obtained crystalline ε-caprolactam was analyzed as described above. As a result, the purity of ε-caprolactam was 99.98%, the contents of cyclohexanone oxime, MTHI and OHP were all less than the limit of detection, the content of caprenolactams was 133 ppm, the UV ray transmittances at 290 nm and 315 nm were 85.2% and 88.3%, respectively, the PM value was 36, the VB was 6.7 ppm, and the pH value was 6.0.

Then, a hydrogenation catalyst (granular 2% palladium/activated carbon catalyst) (0.9 g) was filled in a stainless steel tube having an inner diameter of 6 mm. The height of the catalyst layer was 70 mm. The obtained crystalline ε-caprolactam was heated and molten at 80° C. and was fed into the tube reactor at a rate of about 4.8 g/hr. while allowing a hydrogen gas to flow at a flow rate of 3 cc/min. under a hydrogen pressure of 5 kg/cm$^2$ (0.5 MPa). The total amount of fed ε-caprolactam was about 23 kg. During this period of hydrogenation, the reaction was carried out while raising the catalyst temperature from 80° C. to 95° C. The PM value of the resulting ε-caprolactam was between 0.3 and 2.5.

At the same time when about 6 kg of the crude ε-caprolactam was hydrogenated by the above process, 1.5 kg of the resulting ε-caprolactam after hydrogenation and 0.42 g of sodium hydroxide were charged into a 3 liter distillation apparatus equipped with a Claisen tube, and were distilled under a reduced pressure of about 1 mmHg, to obtain an ε-caprolactam (1.485 kg). The yield thereof was 99%. The obtained ε-caprolactam was analyzed as described above. As a result, the purity of ε-caprolactam was 99.997%, the contents of cyclohexanone oxime, MTHI and OHP were all less than the limit of detection, the content of caprenolactams was 6 ppm, the UV ray transmittances at 290 nm and 315 nm were 99.5% and 99.8%, respectively, the PM value was 0.8, the VB was 1.7 ppm, the FB was 0.02 meq/kg, and the pH value was 5.9.

As the time when about 22 to about 23 kg (in total) of the crude ε-caprolactam was hydrogenated by the above process, 500.2 g of the resulting ε-caprolactam after hydrogenation and 0.14 g of sodium hydroxide were charged into a 1 liter distillation apparatus equipped with a Claisen tube, and were distilled under a reduced pressure of about 1 mmHg, to obtain an ε-caprolactam (496.7 g). The yield thereof was 99.3%. The obtained ε-caprolactam was analyzed as described above. As a result, the purity of ε-caprolactam was 99.998%, the contents of cyclohexanone oxime, MTHI, OHP and caprenolactams were all less than the limit of detection, the UV ray transmittances at 290 nm and 315 nm were 99.0% and 99.4%, respectively, the PM value was 1.5, the FB was 0.025 meq/kg, and the pH value was 5.96.

EXAMPLE 2

Cyclohexanone oxime was subjected to the Beckmann rearrangement, and the obtained crude ε-caprolactam was distilled in the same manners as those in Example 1 to obtain a crude ε-caprolactam having a purity of 99.20%, which contained 1736 ppm of cyclohexanone oxime, 330 ppm of MTHI, and 248 ppm of OHP according to the GC analysis.

The obtained crude ε-caprolactam (50 g) was dissolved in a mixed solvent of cyclohexane and n-heptane (weight ratio of 1:3) (75 g), and the resulting solution was then cooled while stirring to crystallize an ε-caprolactam. The crystallized ε-caprolactam was collected with a centrifugal separator, and the collected crystalline ε-caprolactam was washed with the above-utilized kind of mixed solvent of cyclohexane and n-heptane (25 g) to obtain an ε-caprolactam crystal (46.32 g). The yield thereof was 92.63%. The obtained crystalline ε-caprolactam was analyzed as described above. As a result, the contents of cyclohexanone oxime, MTHI and OHP were all less than the limit of detection, the content of caprenolactams was 91 ppm, and the pH value was 6.27.

Then, the washed crystalline ε-caprolactam (20 g) and a hydrogenation catalyst (2% palladium/carbon beads catalyst having a diameter of 0.6 mm) (0.10 g) were charged into a 100 cc autoclave, and the resulting solution was stirred under a hydrogen pressure of 5 kg/cm$^2$ (0.5 MPa) at 120° C. for 1 hour. After cooling, the obtained crystalline ε-caprolactam was dissolved in methanol, and the catalyst was removed by filtration. Then, the solution was condensed. The obtained ε-caprolactam solution had the VB of 4.8 ppm, and the PM value of 1.5.

The obtained solution of ε-caprolactam was then distilled with a distillation apparatus equipped with a Clainsen tube under reduced pressure to obtain an ε-caprolactam. The ε-caprolactam was analyzed as described above. As a result, the contents of cyclohexanone oxime, MTHI and OHP were all less than the limit of detection, the content of caprenolactams was 12 ppm, the UV ray transmittances at 290 nm and 315 nm were 98.8% and 98.6%, respectively, the PM value was 0.5, the VB was 2.7 and the pH value was 6.45.

EXAMPLE 3

Cyclohexanone oxime was subjected to the Beckmann rearrangement, and the obtained crude ε-caprolactam was distilled in the same manners as those in Example 1 to obtain a crude ε-caprolactam having a purity of 99.08%, which contained 188 ppm of cyclohexanone oxime, 469 ppm of MTHI, and 205 ppm of OHP according to the GC analysis.

Heptane (82.5 g) was added to the distilled ε-caprolactam (55 g) and the resulting solution was maintained at 70° C. Separately, heptane (82.5 g) was cooled with ice.

Then, the mixture of ε-caprolactam and heptane maintained at 70° C., and the ice-cooled heptane were concurrently dropwise added into a flask maintained at 58° C. over 10 minutes to precipitate an ε-caprolactam. After 30 minutes, the precipitated ε-caprolactam crystal was collected with a centrifugal separator, and the collected crystalline ε-caprolactam was washed with heptane (27.5 g) to obtain an ε-caprolactam crystal (34.76 g). The yield thereof was 63.2%. The obtained crystalline ε-caprolactam was analyzed as described above. As a result, the purity of ε-caprolactam was 99.98%, the content of cyclohexanone oxime, MTHI and OHP were all less than the limit of detection, the content of caprenolactams was 173 ppm.

The obtained crystalline ε-caprolactam (28 g) was molten under a nitrogen atmosphere, and was then supplied (under a hydrogen pressure of 5 kg/cm$^2$ (0.5 MPa)) at a space velocity WHSV of 5.3 to 6.6 h$^{-1}$ into a catalyst layer packed with a hydrogenation catalyst (particles of 2% Pd/activated carbon catalyst) (0.9 g) together with a hydrogen gas flown at a flow rate of 3 cc/min. The resulting effluent was distilled under a reduced pressure to obtain a ε-caprolactam (25.5 g). The obtained ε-caprolactam was analyzed as described above. As a result, the purity of ε-caprolactam was 99.99%, the contents of cyclohexanone oxime, MTHI and OHP were all less than the limit of detection, the content of caprenolactams was 14 ppm, the UV ray transmittances at 290 nm and 315 nm were 98.2% and 99.0%, respectively, the PM value was 4.4, the FB was 0.065 meq/kg, and the pH value was 5.99.

EXAMPLE 4

Cyclohexanone oxime was subjected to the Beckmann rearrangement, and the obtained crude ε-caprolactam was distilled in the same manners as those in Example 1 to obtain a crude ε-caprolactam having a purity of 98.32%, which contained 1542 ppm of cyclohexanone oxime, 775 ppm of MTHI, and 423 ppm of OHP according to the GC analysis.

The obtained crude ε-caprolactam (66 g) was dissolved in a mixed solvent of toluene and isooctane (weight ratio of 9.7:90.3) (101.3 g) at 65° C. Separately, the same kind of mixed solvent (41.25 g) was prepared in a dropping funnel and was cooled with ice.

Separately, the same kind of another mixed solvent (41.25 g) was poured into a flask maintained at 52° C. Into the flask, the mixture of ε-caprolactam maintained at 65° C. and the ice-cooled mixed solvent were concurrently dropwise added over 10 minutes to precipitate an ε-caprolactam. After 30 minutes, the precipitated ε-caprolactam crystal was collected with a centrifugal separator maintained at 52° C., and the collected crystalline ε-caprolactam was washed with the above-utilized mixed solvent of toluene and isooctane (27.5 g). The obtained ε-caprolactam crystal was dried under reduced pressure to obtain crystalline ε-caprolactam (42.18 g). The obtained crystalline ε-caprolactam was analyzed as described above. As a result, the purity of ε-caprolactam was 99.97%, the content of cyclohexanone oxime was 4.7 ppm, the contents of MTHI and OHP were less than the limit of detection, the content of caprenolactams was 184 ppm, the PM value was 50.9, the FB was 0.03 meq/kg, and the pH value was 5.95.

The obtained crystalline ε-caprolactam (35 g) was molten at 80° C. under a nitrogen atmosphere, and was supplied (under hydrogen pressure of 5 kg/cm$^2$ (0.5 MPa)) at a space velocity WHSV of 5 h$^{-1}$ into a catalyst layer packed with a hydrogenation catalyst (particles of 2% Pd/activated carbon catalyst) (0.9 g) together with a hydrogen gas flown at a flow rate of 3 cc/min. to obtain an ε-caprolactam. The obtained ε-caprolactam was analyzed as described above. As a result, the purity of ε-caprolactam was 99.997%, the content of cyclohexanone oxime, MTHI and OHP were all less than the limit of detection, the content of caprenolactams was 9 ppm, the WV ray transmittances at 290 nm and 315 nm were 97.6% and 98.2%, respectively, the PM value was 1.3, the FB was 0.02 meq/kg, and the pH value was 5.85.

EXAMPLE 5

Cyclohexanone oxime was subjected to the Beckmann rearrangement, and the obtained crude ε-caprolactam was distilled in the same manners as those in Example 1 to obtain a crude ε-caprolactam having a purity of 99.48%, which contained 125 ppm of cyclohexanone oxime, 134 ppm of MTHI, and 427 ppm of OHP according to the GC analysis.

A 100 parts of the obtained crude ε-caprolactam was dissolved in a 150 parts of mixed solvent of cyclohexane and n-heptane (weight ratio of 1:3), and then, the resulting solution was cooled to 53° C., to crystallize an ε-caprolactam. The ε-caprolactam crystal was collected at 53° C. with a centrifugal separator. The collected crystalline ε-caprolactam was washed at 53° C. with a 50 parts of the above-utilized kind of mixed solvent of cyclohexane and n-heptane, to obtain an ε-caprolactam crystal. The recovery yield thereof was 83.1%. The obtained crystalline ε-caprolactam was analyzed as described above. As a result, the purity of ε-caprolactam was 99.98% the content of cyclohexanone oxime was 4 ppm, the contents of MTHI and OHP were less than the limit of detection, the content of caprenolactams was 201 ppm.

The obtained crystalline ε-caprolactam was molten under a nitrogen atmosphere, and was supplied (under hydrogen pressure of 5 kg/cm$^2$ (0.5 MPa)) at 80° C. at a space velocity WHSV of 5,25, or 50 h$^{-1}$ (respectively, in each batch) into a catalyst layer packed with a hydrogenation catalyst (particles of 2% Pd/activated carbon catalyst, which had been utilized in a hydrogenation for 3 months) (4.0 g) in a stainless steal tube having an inner diameter of 6 mm, together with a hydrogen gas flown at a flow rate of 6 cc/min. The effluent (the ε-caprolactam after hydrogenation) was distilled in a distillation apparatus equipped with Claisen tube under reduced pressure of about 1 mmHg, to obtain an ε-caprolactam. The obtained ε-caprolactam was analyzed as described above. The obtained data, i.e. the purity of ε-caprolactam, the contents of cyclohexanone oxime, MTHI, OHP and caprenolactams, and the PM value, are shown in the following Table 1.

TABLE 1

| Space velocity (WHSV) | Purity of ε-caprolactam | Cyclohexanone oxime | MTHI | OHP | Caprenolactams | PM value |
|---|---|---|---|---|---|---|
| 5h$^{-1}$ | 99.997% | N.D.* | N.D.* | N.D.* | 5 ppm | 0.6 |
| 25h$^{-1}$ | 99.997% | N.D.* | N.D.* | N.D.* | 17 ppm | 4.1 |
| 50h$^{-1}$ | 99.994% | N.D.* | N.D.* | N.D.* | 42 ppm | 12.8 |

*: Less than the limit of detection.

COMPARATIVE EXAMPLE 1

Cyclohexanone oxime was subjected to the Beckmann rearrangement, and the obtained crude ε-caprolactam was distilled in the same manners as those in Example 1 to obtain a crude ε-caprolactam having a purity of 98.993%, which contained 1100 ppm of cyclohexanone oxime, 433 ppm of MTHI, and 208 ppm of OHP according to the GC analysis.

The obtained crude ε-caprolactam (55.05 g) was dissolved in a mixed solvent of cyclohexane and n-heptane (weight ratio of 1:3) (82.5 g) at about 60° C., and charged in a dropping funnel maintained at about 60° C. Separately, a mixed solvent of cyclohexane and n-heptane (weight ratio of 1:3) (41.25 g) was charged in another dropping funnel maintained at about 5° C.

Separately a mixed solvent of cyclohexane and n-heptane (weight ratio of 1:3) (41.25 g) was poured in a flask. Into the flask, the mixture in the dropping funnel maintained at about 60° C., and the mixed solvent in the dropping funnel maintained at about 5° C. were concurrently dropwise added at 50° C. over 10 minutes while stirring at 350 rpm. After 2 minutes, a slight amount of ε-caprolactam crystal was added to the mixture as a seed crystal. The mixture was stirred for 30 minutes, and the precipitated ε-caprolactam crystal was collected with a centrifugal separator maintained at 50° C. The collected ε-caprolactam was washed with the above-utilized kind of mixed solvent (27.5 g) and was dried under reduced pressure to obtain a crystalline ε-caprolactam (42.95 g). The obtained crystalline ε-caprolactam was analyzed as described above. As a result, the purity of ε-caprolactam was 99.980%, the content of cyclohexanone oxime was 7.4 ppm, the contents of MTHI and OHP were less than the limit of detection, the content of caprenolactams was 165 ppm, the PM value was 51, and the FB was 0.033 meq/kg.

The obtained crystalline ε-caprolactam (35.00 g) was dissolved in a mixed solvent of cyclohexane and n-heptane (weight ratio of 1:3) (52.5 g) at about 60° C., and the resulting solution was charged in a dropping funnel maintained at about 60° C. Separately, a mixed solvent of cyclohexane and n-heptane (weight ratio of 1:3) (26.25 g) was charged in a dropping funnel maintained at about 5° C.

Separately, a mixed solvent of cyclohexane and n-heptane (weight ratio of 1:3) (26.25 g) was poured in a flask. Into the flask the mixture in the dropping funnel maintained at about 60° C., and the mixed solvent in the dropping funnel maintained at about 5° C. were concurrently dropwise added at 50° C. over 10 minutes while stirring at 350 rpm. After 2 minutes, a slight amount of ε-caprolactam crystal was added to the mixture as a seed crystal. The mixture was stirred for 30 minutes, and the precipitated ε-caprolactam crystal was collected with a centrifugal separator maintained at 50° C. The collected ε-caprolactam was washed with the above-utilized kind of mixed solvent (27.5 g) and was dried under reduced pressure to obtain a crystalline ε-caprolactam (22.55 g). The obtained crystalline ε-caprolactam was analyzed as described above. As a result, the purity of ε-caprolactam was 99.986%, the content of cyclohexanone oxime was 4.1 ppm, the contents of MTHI and OHP were less than the limit of detection, the content of caprenolactams was 84 ppm, the PM value was 24.7, and the FB was 0.031 meq/kg.

COMPARATIVE EXAMPLE 2

Cyclohexanone oxime was subjected to the Beckmann rearrangement, and the obtained crude ε-caprolactam was distilled in the same manners as those in Example 1 to obtain a crude ε-caprolactam having a purity of 99.33%, which contained 451 ppm of cyclohexanone oxime, 240 ppm of MTHI, 476 ppm of OHP, and 1524 ppm of caprenolactams according to the GC analysis.

The obtained crude ε-caprolactam was dissolved in the same weight of water, and the solution was shaken with 2.33 times weight of cyclohexane for 30 minutes and the resulting mixture was kept standing for 15 minutes to separate phases. The obtained aqueous phase was extracted eight times with the same volume of cyclohexane. The aqueous phase was concentrated to obtain an extracted ε-caprolactam (recovery of 81.6%). The extracted ε-caprolactam was analyzed as described above. As a result, the purity of ε-caprolactam was 99.76%, the content of cyclohexanone oxime was 133 ppm, the content of MTHI was 211 ppm, the content of OHP was less than the limit of detection, the content of caprenolactams was 532 ppm, the UV ray transmittances at 290 nm and 315 nm were 32.4% and 52.9%, respectively, the PM value was 198, the FB was 2.5 meq/kg, and the pH value was 8.42.

Then, a hydrogenation catalyst (2% palladium/activated carbon catalyst) (4.0 g) was filled in a stainless steel tube having an inner diameter of 6 mm. The extracted ε-caprolactam (110 g) was flowed in the tube reactor by an upflow mode at a rate of about 0.34 ml/hr. while allowing a hydrogen gas to flow at a flow rate of 6 cc/min. under a hydrogen pressure of 5 kg/cm$^2$ (0.5 MPa) at 80° C. to obtain an ε-caprolactam. The obtained ε-caprolactam was analyzed as described above. As a result, the purity of ε-caprolactam was 99.77%, the content of cyclohexanone oxime was 157 ppm, the content of MTHI was 156 ppm, the contents of OHP and caprenolactams were less than the limit of detection, the UV ray transmittances at 290 nm and 315 nm were 57.5% and 67.4%, respectively, and the PM value was 17.

The obtained ε-caprolactam (79.3 g) was then distilled with a 200 ml distillation apparatus equipped with a Clainsen tube under a reduced pressure of about 1 mmHg to obtain an ε-caprolactam (78.3 g). The yield thereof was 99%. The obtained ε-caprolactam was analyzed as described above. As a result, the purity of ε-caprolactam was 99.85%, the content of cyclohexanone oxime was 123 ppm, the content of MTHI was 127 ppm, the contents of OHP and caprenolactams were less than the limit of detection, the UV ray transmittances at 290 nm and 315 nm were 85.5% and 91.5%, respectively, the PM value was 6.3, the FB was 2.0 meq/kg, and the pH value was 9.6.

COMPARATIVE EXAMPLE 3

Cyclohexanone oxime was subjected to the Beckmann rearrangement, and the obtained crude ε-caprolactam was distilled in the same manners as those in Example 1 to obtain a crude ε-caprolactam having a purity of 99.47%, which contained 314 ppm of cyclohexanone oxime, 213 ppm of MTHI, and 176 ppm of OHP according to the GC analysis.

The obtained crude ε-caprolactam (55.05 g) was dissolved in a mixed solvent of cyclohexane and n-heptane (weight ratio of 1:3) (165 g) at about 60° C., and the resulting solution was cooled to 50° C. over 10 minutes while stirring at 350 rpm, and then a slight amount of ε-caprolactam crystal was added to the solution, to crystallize ε-caprolactam. After stirring for 30 minutes, the ε-caprolactam crystal was collected with a centrifugal separator maintained at 50° C. The collected ε-caprolactam was washed with the above-utilized kind of mixed solvent (27.5 g) and was dried under reduced pressure, to obtain a crystalline ε-caprolactam (42.81 g). The obtained crystalline ε-caprolactam was analyzed as described above. As a result, the purity of ε-caprolactam was 99.981%, the contents of cyclohexanone oxime was 3 ppm, the contents of MTHI and OHP were less than the limit of detection, the content of caprenolactams was 140 ppm, the PM value was 39, and the FB was 0.048 meq/kg.

The obtained crystalline ε-caprolactam (35.00 g) was dissolved in a mixed solvent of cyclohexane and n-heptane (weight ratio of 1:3) (105 g) at about 60° C., and the resulting solution was cooled to 50° C. over 10 minutes while stirring at 350 rpm, and then a slight amount of ε-caprolactam crystal was added to the solution, to crystallize ε-caprolactam. After stirring for 30 minutes, the ε-caprolactam crystal was collected with a centrifugal separator maintained at 50° C. The collected ε-caprolactam was washed with the above-utilized kind of mixed solvent (27.5 g) and was dried under reduced pressure, to obtain a crystalline ε-caprolactam (28.58 g). The obtained crystalline ε-caprolactam was analyzed as described above. As a result, the purity of ε-caprolactam was 99.994%, the contents of cyclohexanone oxime, MTHI and OHP were all less than the limit of detection, the content of caprenolactams was 51 ppm, the PM value was 12, and the FB was 0.042 meq/kg.

What is claimed is:

1. A process for preparing ε-caprolactam comprising the steps of:

crystallizing an ε-caprolactam from a hydrocarbon solution containing a crude ε-caprolactam to obtain a crystallized ε-caprolactam having a free basicity of 0.25 meg/kg or less, and allowing the crystallized ε-caprolactam in contact with hydrogen in the presence of a hydrogenation catalyst.

2. The process according to claim 1, wherein said hydrocarbon solution contains at least one hydrocarbon selected from the group consisting of linear aliphatic hydrocarbons having 6 to 12 carbon atoms, side-chain aliphatic hydrocarbons having 6 to 12 carbon atoms and alicyclic hydrocarbons having 6 to 12 carbon atoms.

3. The process according to claim 1, wherein said crude ε-caprolactam is prepared by allowing cyclohexanone oxime in contact with a zeolite solid catalyst in a gas phase.

4. The process according to claim 1, wherein obtained ε-caprolactam contains less than 10 ppm of cyclohexanone oxime, less than 10 ppm of 1,2,3,4,6,7,8,9-octahydrophenazine, less than 25 ppm of 3-N-methyl-4,5,6,7-tetrahydrobenzimidazole, and less than 30 ppm of caprenolactams.

5. The process according to claim 1, wherein said crude ε-caprolactam contains at least 30 ppm of caprenolactams, and at least one impurity selected from the group of at least 10 ppm of cyclohexanone oxime, at least 10 ppm of 1,2,3,4,6,7,8,9-octahydrophenazine and at least 25 ppm of 3-N-methyl-4,5,6,7-tetrahydrobenzimidazole.

6. The process according to claim 1, wherein ε-caprolactam after crystallization has a pH value of 6.5 or less.

7. The process according to claim 1, wherein ε-caprolactam after hydrogenation has a PM value of less than 10.

8. The process according to claim 1, wherein said crystallized ε-caprolactam is allowed in contact with hydrogen for 0.033 to 2 hours or at a space velocity of 0.5 to 30 $h^{-1}$.

9. A process for preparing ε-caprolactam comprising the steps of:

crystallizing an ε-caprolactam from a hydrocarbon solution containing a crude ε-caprolactam to obtain a crystallized ε-caprolactam having a pH value of 6.5 or less, and allowing the crystallized ε-caprolactam in contact with hydrogen in the presence of a hydrogenation catalyst.

10. A process for preparing ε-caprolactam comprising the steps of:

crystallizing an ε-caprolactam at a temperature of from about 10° C. to less than the melting point of ε-caprolactam from a hydrocarbon solution containing a crude ε-caprolactam, and allowing the crystallized ε-caprolactam in contact with hydrogen in the presence of a hydrogenation catalyst.

11. The process according to claim 10, wherein a crystallization temperature is from about 30° C. to about 60° C.

* * * * *